United States Patent [19]

Hoehn

[11] 4,248,878
[45] Feb. 3, 1981

[54] IMIDAZOLE DERIVATIVES OF 1,5,6,11-TETRAHYDROBENZO[5,6]CY-CLOHEPTA[1,2-b]PYRAZOLO[4,3-e]PYRIDINES

[75] Inventor: Hans Hoehn, Tegernheim, Fed. Rep. of Germany

[73] Assignee: E. R. Squibb & Sons, Inc., Princeton, N.J.

[21] Appl. No.: 86,019

[22] Filed: Oct. 17, 1979

[51] Int. Cl.³ .................... C07D 471/04; A61K 31/44
[52] U.S. Cl. ........................................ 424/267; 546/64
[58] Field of Search ........................... 546/64; 424/267

[56] References Cited

U.S. PATENT DOCUMENTS

| 3,764,609 | 10/1973 | Vander Stelt | 260/309 |
| 3,778,447 | 12/1973 | Draber et al. | 260/309 |
| 4,013,672 | 3/1977 | Hoehn | 546/64 |
| 4,062,858 | 12/1977 | Hoehn et al. | 424/267 |
| 4,169,205 | 9/1979 | Hoehn | 548/336 |
| 4,179,564 | 12/1979 | Hoehn et al. | 546/64 |

Primary Examiner—Mark L. Berch

Attorney, Agent, or Firm—Lawrence S. Levinson; Burton Rodney

[57] ABSTRACT

New imidazole derivatives of 1,5,6,11-tetrahydrobenzo[5,6]cyclohepta[1,2-b]pyrazolo[4,3-e]-pyridines have the general formula

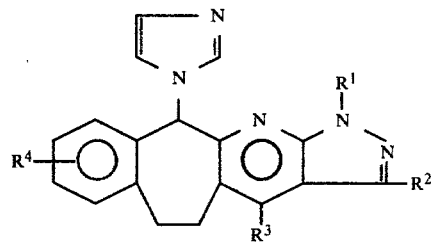

wherein $R^1$ and $R^2$ may be the same or different and each may be hydrogen, lower alkyl, phenyl-lower alkyl, phenyl or substituted phenyl, and $R^3$ and $R^4$ may be the same or different and each may be hydrogen, halogen, lower alkyl, or lower alkoxy. They and the salts thereof are useful as antimicrobial agents, and in particular as antifungal agents.

8 Claims, No Drawings

IMIDAZOLE DERIVATIVES OF 1,5,6,11-TETRAHYDROBENZO[5,6]CYCLOHEPTA[1,2-b]PYRAZOLO[4,3-e]PYRIDINES

SUMMARY OF THE INVENTION

This invention relates to new imidazole derivatives of 1,5,6,11-tetrahydrobenzo [5,6]cyclohepta[1,2-b]pyrazolo [4,3-e]pyridines as well as salts thereof. These new compounds have the general formula

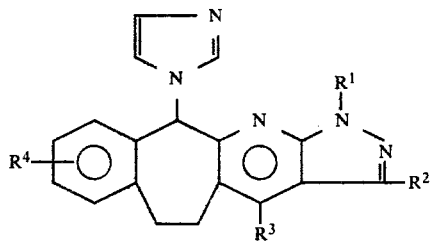

wherein $R^1$ and $R^2$ may be the same or different and each may be hydrogen, lower alkyl, phenyl-lower alkyl, phenyl or substituted phenyl wherein the phenyl group bears one halogen, hydroxy, lower alkoxy, lower alkyl, lower alkylthio, cyano or nitro group; $R^3$ and $R^4$ may be the same or different and each may be hydrogen, halogen, lower alkyl or lower alkoxy.

The new compounds of formula I and their salts are useful as antifungal and antibacterial agents.

DETAILED DESCRIPTION OF THE INVENTION

The lower alkyl groups include straight or branched chain hydrocarbon groups containing 1 to 7 carbon atoms. Examples include methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$–$C_4$, especially $C_1$–$C_2$, lower alkyl groups are preferred.

The halogens are the four common halogens, chlorine and bromine being preferred in that order. Preferably, but not necessarily, all halogens in a single compound are the same.

Preferred embodiments of this invention are compounds of formula I wherein $R^1$ is lower alkyl, such as methyl or ethyl and $R^2$, $R^3$ and $R^4$ are hydrogen.

The compounds of formula I are prepared by N-cycloalkylation of an imidazole of the formula

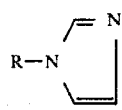

wherein R is hydrogen or a metal like sodium or potassium, with an appropriate reactive ester of the formula

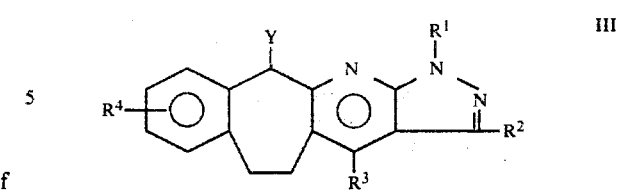

wherein y is a reactive ester function, such as halo, mesyl, tosyl or the like.

Another method, which can be effected without preparing the ester of formula III, is the reaction of the alcohol of the formula

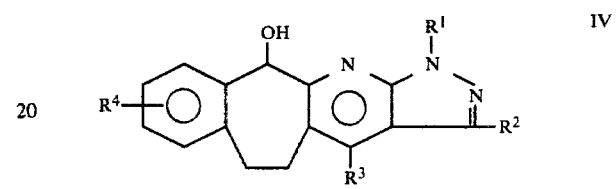

with thionyl-bis-imidazole or carbonyl-bis-imidazole of the formula

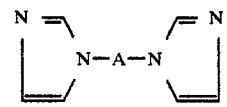

wherein A represents —SO— or —CO—.

The 11-chloro derivative (y=Cl) of formula III and the 11-hydroxy derivative of formula IV, respectively, may be prepared according to the procedure reported in U.S. Pat. No. 4,111,940 (e.g., Example 2; Example 44a).

The compounds of formula I form salts which are also part of this invention. The salts include acid-addition salts, particularly the non-toxic, physiologically acceptable members. The bases of formula I form salts by reactions with one or more equivalents of any of a variety of the common inorganic and organic acids providing acid addition salts including for example, hydrohalides (especially hydrochloride and hydrobromide), sulfate, nitrate, borate, phosphate, oxalate, tartrate, maleate, citrate, acetate, ascorbate, succinate, benzene-sulfonate, methanesulfonate, cyclohexanesulfamate and toluenesulfonate. The acid addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base, such as barium hydroxide or sodium hydroxide, to obtain the free base of formula I. Other salts may then be formed from the free base by reaction with one or more equivalents of acid containing the desired acid group.

The new compounds of formula I and their salts are useful as anti-fungal and anti-bacterial agents and may be used to combat infections in various mammalian species, such as mice, rats, dogs, guinea pigs and the like, particularly those due to organisms such as *Candida albicans*, as well as organisms such as *Trichomonas vaginalis* or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg per kg per day in 2 to 4 divided doses. These may be conventionally formulated in a tablet, capsule or elixir containing about 10 to 250 mg per dosage unit, by compounding the active substance or substances with the conventional vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following examples are illustrative of the invention. Temperatures are on the Celsius scale.

EXAMPLE 1

1-Ethyl-1,5,6,11-tetrahydro-11-(1H-imidazol-1-yl)-benzo[5,6]cyclohepta[1,2-b]pyrazolo[4,3-e]pyridine, hydrochloride (1:1)

2.3 g of 11-chloro-1-ethyl-1,5,6,11-tetrahydrobenzo[5,6]cyclohepta[1,2]pyrazolo[4,3-e]pyridine (0.008 mol), dissolved in 50 ml of dry toluene, and 1.7 g of imidazole (0.025 mol) are refluxed for 3.5 hours. Then toluene is removed in vacuo, the residue triturated with water and extracted with ether. The dried ethereal solution is allowed to stand for 3-4 days to separate unreacted compound and side product. To the clear ethereal solution is added, while stirring, ethereal hydrochloric acid. The precipitated hydrochloride (1.3 g; m.p. 106°-109° C.) is recrystallized from ethyl acetate to give the title compound, m.p. 108°-110° C.

EXAMPLES 2 to 15

Following the procedure of Example 1 except substituting for 11-chloro-1-ethyl-1,5,6,11-tetrahydrobenzo[5,6]cyclohepta[1,2]pyrazolo[4,3-e]-pyridine, the compound shown in Column I of Table A below, the product shown in Column II is obtained.

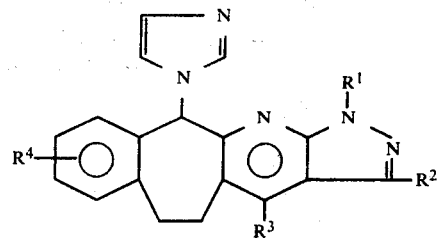

wherein $R^1$ and $R^2$ may be the same or different and each is hydrogen, lower alkyl, phenyl-lower alkyl, phenyl or substituted phenyl wherein the phenyl group bears one halogen, hydroxy, lower alkoxy, lower alkyl, lower alkylthio, cyano or nitro group, and $R^3$ and $R^4$ may be the same or different and each is hydrogen, halogen, lower alkyl or lower alkoxy, and non-toxic physiologically acceptable acid-addition salts thereof.

2. The compound as defined in claim 1 wherein $R^1$ is lower alkyl.

3. The compound as defined in claim 1 wherein $R^2$, $R^3$ and $R^4$ are each hydrogen.

4. The compound as defined in claim 1 wherein $R^1$ is lower alkyl, and $R^2$, $R^3$ and $R^4$ are each hydrogen.

5. The compound as defined in claim 1 in the form of its hydrochloride salt.

6. The compound as defined in claim 4 having the name 1-ethyl-1,5,6,11-tetrahydro-11-(1H-imidazol-1-yl)benzo[5,6]cyclohepta[1,2-b]pyrazolo[4,3e]-pyridine or its hydrochloride salt.

7. An antimicrobial composition consisting essentially of an antimicrobially effective amount of a compound as defined in claim 1 and a pharmaceutically acceptable carrier therefor.

8. A method for treating bacterial or fungal infections in mammals which comprises administering to a mammalian host an effective amount of a composition as defined in claim 7.

TABLE A

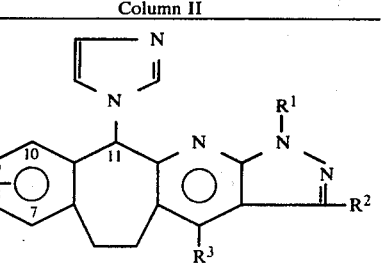

| Ex. No. | Y | $R^1$ | $R^2$ | $R^3$ | $R^4$ (position) | $R^1$ | $R^2$ | $R^3$ | $R^4$ (position) |
|---|---|---|---|---|---|---|---|---|---|
| 2. | Cl | H | H | H | H | | | | |
| 3. | Br | CH$_3$ | H | H | Cl(9) | | | | |
| 4. | Cl | C$_2$H$_5$ | C$_2$H$_5$ | H | CH$_3$(8) | | as in Column I | | |
| 5. | Br | C$_6$H$_5$CH$_2$ | H | H | CH$_3$O(7) | | | | |
| 6. | tosyl | H | C$_6$H$_5$(CH$_2$)$_2$ | Br | Br(10) | | | | |
| 7. | mesyl | C$_6$H$_5$ | C$_6$H$_5$ | Cl | H | | | | |
| 8. | Cl | H | C$_6$H$_5$ | C$_2$H$_5$ | H | | | | |
| 9. | Br | C$_6$H$_5$ | H | n-C$_3$H$_7$ | H | | | | |
| 10. | Cl | p-ClC$_6$H$_4$ | H | C$_2$H$_5$O | H | | | | |
| 11. | Br | p-CH$_3$SC$_6$H$_4$ | p-CH$_3$C$_6$H$_4$ | H | H | | | | |
| 12. | tosyl | m-CH$_3$OC$_6$H$_5$ | H | H | H | | | | |
| 13. | mesyl | o-ClC$_6$H$_4$ | H | CH$_3$ | CH$_3$(8) | | | | |
| 14. | Cl | H | p-NO$_2$C$_6$H$_4$ | H | H | | | | |
| 15. | Br | H | p-CNC$_6$H$_4$ | H | H | | | | |

What is claimed is:

1. A compound of the formula

* * * * *